United States Patent [19]

Voloshin et al.

[11] Patent Number: 5,731,411
[45] Date of Patent: Mar. 24, 1998

[54] PROMOTION OF HOMOLOGOUS DNA PAIRING BY RECA-DERIVED PEPTIDES

[75] Inventors: Oleg Voloshin, Kensington; Lijiang Wang, Rockville; R. Daniel Camerini-Otero, Kensington, all of Md.

[73] Assignee: The United States of America as represented by the Department of Health and Human Services, Washington, D.C.

[21] Appl. No.: 483,115

[22] Filed: Jun. 7, 1995

Related U.S. Application Data

[63] Continuation-in-part of Ser. No. 89,910, Jul. 12, 1993, Pat. No. 5,460,941, and a continuation-in-part of Ser. No. 97,831, Jul. 26, 1993, Pat. No. 5,510,473.

[51] Int. Cl.⁶ .......................... C07K 17/08; A61K 38/10
[52] U.S. Cl. ............................. 530/326; 530/300
[58] Field of Search ............................. 530/300, 326

[56] References Cited

U.S. PATENT DOCUMENTS

| | | | |
|---|---|---|---|
| 4,736,866 | 4/1988 | Leder et al. | 800/1 |
| 5,460,941 | 10/1995 | Camerini-Otero et al. | 435/6 |
| 5,510,473 | 4/1996 | Camerini-Otero et al. | 530/23.5 |

OTHER PUBLICATIONS

B. Alberts, et al. (1989), *Molecular Biology Of The Cell*, Second Edition, Garland Publishing, Inc., New York, p. 980.
C.R. Bartram, et al. (1983) "Translocation of c–abl Oncogene Correlates with the Presence of a Philadelphia Chromosome in Chronic Myelocytic Leukaemia", *Nature*, 306(17):277–280.
R.D. Camerini–Otero, et al. (1993) "Parallel DNA Triplexes, Homologous Recombination, and Other Homology–Dependent DNA Interactions", *Cell*, 73:217–223.
A.J. Clark, et al. (1965) "Isolation and Characterization of Recombination–Deficient Mutants of *Escherichia coli* K12", *Proc. N. A. S.*, 53:451–459.
M.M. Cox (1993) "Relating Biochemistry to Biology: How the Recombinational Repair Function of RecA Protein is Manifested in Its Molecular Properties", *BioEssays*, 15(9):617–623.
J. Groffen, et al. (1984) "Philadelphia Chromosomal Breakpoints are Clustered within a Limited Region, bcr, on Chromosome 22", *Cell*, 36:93–99.

H. Hayatsu, et al. (1967) "The Selective Degradation of Pyrimidines in Nucleic Acids by Permanganate Oxidation", *Biochem. And Biophys. Res. Communications*, 29(4):556–561.
Th. Koller, et al. (1983) "Complexes of recA Protein with Single Stranded DNA" *Mech. of DNA Replication and Recombination*, 723–729.
S.C. Kowalczykowski, et al. (1994) "Homologous Pairing and DNA Strand–Exchange Proteins", *Annu. Rev. Biochem.*, 63:991–1043.
R. Kurzrock, et al. (1987) "A Novel c–abl Protein Product in Philadelphia–Positive Acute Lymphoblastic Leukaemia" *Nature*, 325(12):631–635.
S.L. Mansour (1990) "Gene Targeting in Murine Embryonic Stem Cells: Introduction of Specific Alterations into the Mammalian Genome", *GATA*, 7(8):219–227.
A.M. Maxam, et al. (1977) "Sequencing End–Labeled DNA with Base–Specific Chemical Cleavages", *Methods in Enzymology*, 65:499–560.
A.I. Roca, et al. (1990) "The RecA Protein: Structure and Function", *Biochemistry and Mol. Biology*, 415–456.
R.M. Story, et al. (1992) "The Structure of the *E. coli* recA Protein Monomer and Polymer", *Nature*, 355:318–325.
R.M. Story, et al. (1993) "Structural Relationship of Bacterial RecA Proteins to Recombination Proteins from Bacteriophage T4 and Yeast", *Science*, 259:1892–1896.
I. Wong, et al. (1993) "A Double–Filter Method for Nitrocellulose–Filter Binding: Application to Protein–Nucleic Acid Interactions", *Proc. Natl. Acad. Sci. USA*, 90:5428–5432.
R.W. Woody, et al. (1985) "Circular Dichroism of Peptides", *The Peptides*, 7:15–114.
Maraboeuf et al 1995 J. Biol. Chem. 270(52):30927–30932.
Gardner et al 1995 Eur. J. Biochem. 233:419–425.
Voloshin et al 1996 Science 272:868–872.

*Primary Examiner*—Karen C. Carlson
*Attorney, Agent, or Firm*—Knobbe, Martens, Olson & Bear, LLP

[57] ABSTRACT

A peptide having at least 15 consecutive amino acids of the amino acid sequence shown in SEQ ID NO:1 or conservative amino acid substitutions thereof. The peptide is capable of promoting pairing of a single-stranded DNA molecule and a double-stranded DNA molecule. The single-stranded DNA molecule is homologous to at least a portion of the double-stranded DNA molecule. The single-stranded DNA molecule and the double-stranded DNA molecule form a three-stranded DNA molecule.

3 Claims, 9 Drawing Sheets

FECO    NQIRMKIGVMFGNPETTTGG
WECO    NQIRMKIGVMWGNPETTTGG
YECO    NQIRMKIGVMYGNPETTTGG
HECO    NQIRMKIGVMHGNPETTTGG
AECO    NQIRMKIGVMAGNPETTTGG
WT-14       RMKIGVMFGNPETT
WT-Scr  IPEQTKGGRNTMNVFGMGIT

FIG. 1A

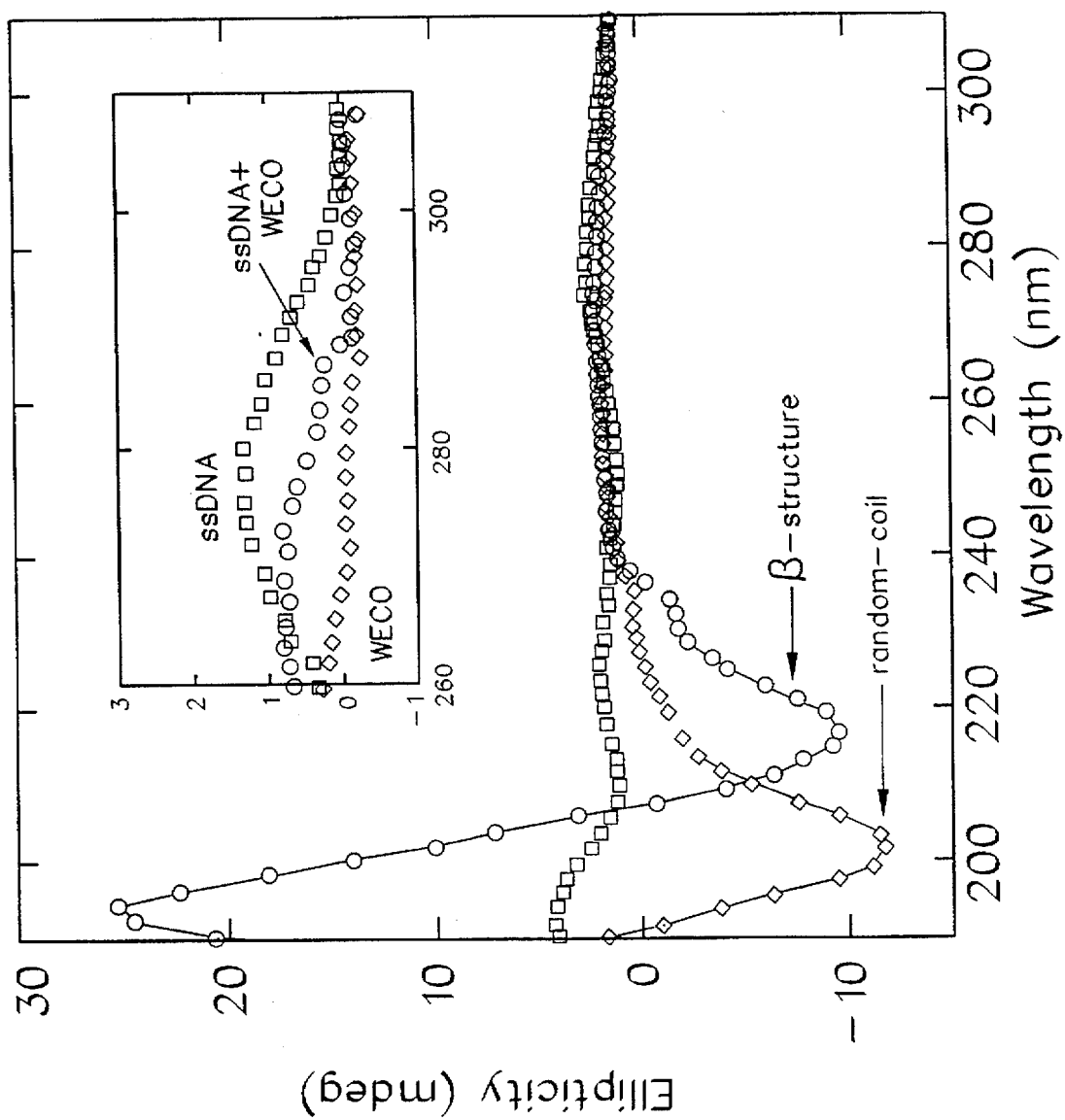

PROMOTION OF HOMOLOGOUS DNA PAIRING BY RECA-DERIVED PEPTIDES

CROSS-REFERENCE TO RELATED APPLICATIONS

This application is continuation-in-part of U.S. application Ser. No. 08/089,910, filed Jul. 12, 1993, now U.S. Pat. No. 5,460,941; and is also a continuation-in-part of U.S. application Ser. No. 08/097,831, filed Jul. 26, 1993, now 5,510,473. The complete disclosures of both of these related applications is hereby incorporated herein by this reference thereto.

FIELD OF THE INVENTION

The present invention relates to peptides capable of promoting homologous DNA pairing and the use of the compositions containing the peptides in promoting such DNA pairing. More specifically, the invention relates to short peptides derived from the E. coli recA protein which are capable of catalyzing homologous DNA pairing.

BACKGROUND OF THE INVENTION

RecA proteins play an essential role in homologous DNA recombination pathways (Cox et al., Bioessays, 15:617–623, 1993; Kowalczykowski et al., Ann. Rev. Biochem., 63:991–1044, 1994). The first RecA protein was purified from E. coli in 1965 by Clark et al. (Proc. Natl. Acad. Sci. USA, 53:451, 1965) and since then has been isolated and cloned from many other prokaryotic organisms (Roca et al., Biochem. Mol. Biol., 25:415–456, 1990). The RecA protein is a 38 kD polypeptide which possesses a multitude of biochemical activities.

RecA promotes homologous DNA recombination via a multi-step pathway involving the formation of a single-stranded nucleoprotein filament, DNA pairing and subsequent strand exchange to form heteroduplex DNA. RecA is directly involved in post-replication DNA repair and the induction of the SOS response by cleavage of the lexA repressor protein. RecA mediates a set of DNA strand exchange reactions in vitro by self-assembly into filaments, binding to both single-stranded DNA (ssDNA) and double-stranded DNA (dsDNA), and hydrolysis of ATP. Although the crystal structure of the protein has been solved (Story et al., Nature, 355:318–325, 1992), the precise domain(s) which catalyze the pairing of two homologous DNA molecules are unknown. RecA binds to ssDNA, forming a nucleoprotein (presynaptic) filament that is the homology searching moiety that mediates the pairing with a target DNA duplex.

SUMMARY OF THE INVENTION

One embodiment of the present invention is a peptide comprising at least 15 consecutive amino acids of the amino acid sequence shown in SEQ ID NO:1 or conservative amino acid substitutions thereof, the peptide being capable of promoting pairing of a single-stranded DNA molecule and a double-stranded DNA molecule, wherein the single-stranded DNA molecule is homologous to at least a portion of the double-stranded DNA molecule. Preferably, the peptide has the amino acid sequence shown in SEQ ID NO:1. Alternatively, the peptide has an amino acid sequence shown in SEQ ID NO:2 or SEQ ID NO:3.

Another embodiment of the invention is a method for selectively targeting a single-stranded DNA molecule to a double-stranded DNA molecule containing at least a portion of a sequence homologous to the single-stranded DNA molecule, comprising contacting the single-stranded DNA molecule and the double-stranded DNA molecule in the presence of a peptide described above. Advantageously, this peptide has the amino acid sequence shown in SEQ ID NO:1, SEQ ID NO:2 or SEQ ID NO:3. According to another aspect of this preferred embodiment, the targeted DNA region of the double-stranded DNA molecule encodes a mutant form of a protein.

The present invention also provides a method of inhibiting transcription of a specific gene sequence present on one strand of a double-stranded DNA molecule comprising contacting a peptide with the double-stranded DNA molecule and with a single-stranded DNA molecule, which single-stranded DNA molecule is homologous to at least a portion of the gene sequence and hybridizes therewith to form a three-stranded molecule, wherein the peptide is a peptide described above. Preferably, the peptide has the amino acid sequence shown in SEQ ID NO:1, SEQ ID NO:2 or SEQ ID NO:3. Advantageously, the specific gene sequence on the double-stranded DNA molecule encodes a mutant form of a protein. Alternatively, the specific gene sequence on said double-stranded DNA molecule encodes an oncogene or viral transcript.

BRIEF DESCRIPTION OF THE FIGURES

FIG. 1a illustrates the peptides used in DNA binding experiments. FECO is the naturally-occurring sequence of residues 193–212 of E. coli RecA (SEQ ID NO:1). WECO (SEQ ID NO:2), YECO (SEQ ID NO:3), HECO (SEQ ID NO:4) and AECO (SEQ ID NO:5) contain, in place of phenylalanine at position 203, tryptophan, tyrosine, histidine and alanine, respectively. WT-14 is the naturally occurring sequence of residues 196–209 of RecA (amino acids 4–17 of SEQ ID NO:1). WT-Scr (SEQ ID NO:6) is a randomly scrambled sequence having the same amino acid composition as FECO.

FIG. 2b illustrates a CD spectrum of 0.10 mM WECO in the presence or absence of 0.20 mM ssDNA (SEQ ID NO:7) at pH 6.0±0.2. The inset shows the enlargement of the spectral region from 260–300 nm to emphasize the intensity change at 278 nm.

DETAILED DESCRIPTION OF THE INVENTION

Figure 1B:
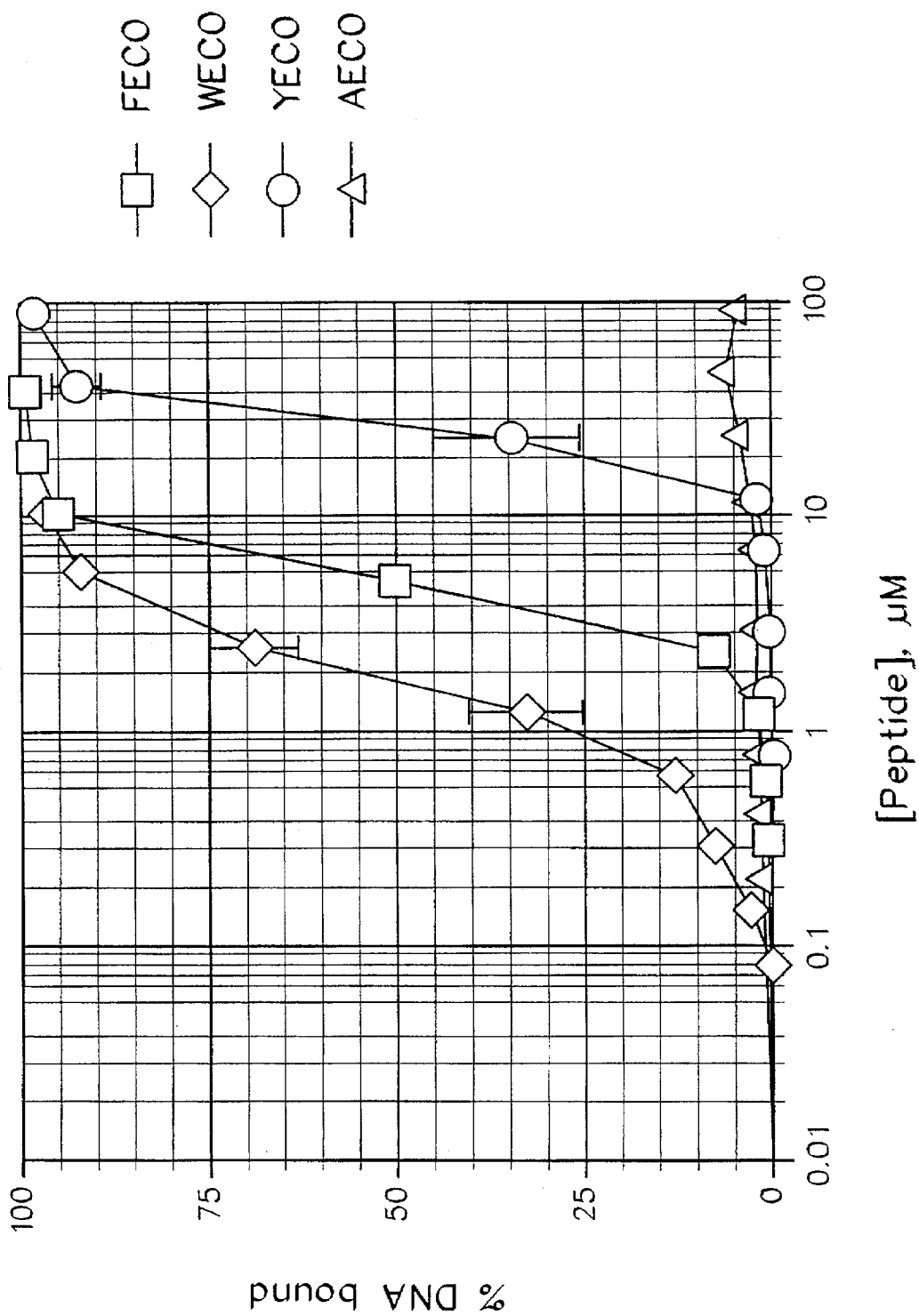
FIG. 1b illustrates binding of the FECO, WECO, YECO and AECO to ssDNA (0.5 µM) in the presence of 10 mM $MgCl_2$. The peptide concentration is shown on the x-axis and the percentage of ss DNA bound is shown on the y-axis.

The sequence-specific targeting of DNA by RecA has important therapeutic applications including site-specific gene inactivation, correction of gene mutations and the control of gene expression. Other applications include sequence-specific mapping and manipulation of complex genomes, particularly the human genome.

Sequence-specific targeting of DNA is described in copending U.S. application Ser. No. 08/089,910. This copending application describes contacting ds DNA with a ss oligonucleotide probe complementary to a specific sequence in the presence of the entire E. coli RecA protein, resulting in triplex formation in vitro.

However, the use of whole, intact RecA protein for specific targeting of DNA presents several drawbacks typically associated with whole proteins. These drawbacks include the difficulty of whole protein uptake by cells, delivery of the protein in sufficient concentration to cells to mediate an effect, generation of a significant antibody response, susceptibility to biodegradation and the difficulty in modifying large proteins to increase their bioactivity. In addition, the production of recombinant protein is labor-intensive and expensive in comparison to the synthesis of small peptides.

Thus, there is a need for a smaller, more stable molecule capable of being easily introduced into cells both in vitro and in vivo for targeting ds DNA in the genome, both for therapeutic and mapping/cloning applications. The present invention addresses this need.

The present invention relates to the discovery that a twenty amino acid peptide spanning the ssDNA binding domain of the homologous recombination-promoting RecA protein binds to both ssDNA and dsDNA, promotes unstacking of the DNA base pairs, and, most importantly, selectively catalyzes the formation of joint ssDNA-dsDNA molecules at a region of homology between the ssDNA and dsDNA. The single-stranded DNA binding domain of E. coli RecA is in a disordered mobile loop in the crystal structure (Gardner et al., Eur. J. Biochem., 1995 (in press). It is quite unexpected that such a short peptide is capable of carrying out the most unique and characteristic reaction mediated by the whole RecA protein: pairing of homologous single- and double-stranded DNA molecules and the formation of joint molecules. It is also quite surprising that these short peptides can mediate such complex reactions, as the native RecA protein has a molecular weight of about 20 times that of the peptide and it would be expected that additional regions of the protein beyond the 20 amino acids would be required for its activity.

The short peptides of the present invention have the sequence of the E. coli single strand binding domain, or sequence variations thereof. As explained in detail hereinbelow, these peptides can selectively target a single-stranded oligonucleotide to a homologous sequence contained in a double-stranded DNA molecule. This selective targeting has therapeutic applications, including inactivation of deleterious genes and control of gene expression, and may be used to map complex genomes, including the human genome.

The 20 amino acid peptide capable of promoting homologous DNA pairing corresponds to amino acids 193–212 of native RecA (SEQ ID NO:1) and variations thereof that retain activity. A variety of such variations on the 20-mer can be made. The synthetic peptides and oligonucleotides described herein were made according to the techniques described below in Example 1.

EXAMPLE 1

Oligonucleotide and Peptide Synthesis

Oligonucleotides were synthesized on an Applied Biosystems model 380B synthesizer and purified by polyacrylamide gel electrophoresis (PAGE). The peptides used in the examples herein were made on an Applied Biosystems model 431A synthesizer, purified by reverse phase high performance liquid chromatography (HPLC) on a C-18 column and dissolved in 20 mM CAPS (3-[Cyclohexylamino]-1-propane-sulfonic acid; Sigma, St. Louis, Mo.), pH 10.6.

The 14-mer, WT-14, described above in the brief description of FIG. 1a, lacks the first three and last three amino acids of the active 20-mer. This 14-mer did not promote the formation of joint DNA molecules. Thus, RecA-derived peptides having 15 amino acids or more, and including amino acids 196–209 (the 14-mer), are within the scope of the invention. Although longer peptides are included within the scope of the present invention, the preferred upper limit of the length of the peptide would be about 50 amino acids, i.e. the 20-mer plus 30 additional residues of native RecA in combination on the N-terminal and/or C-terminal sides of the 20-mer. Peptides longer than about 50 amino acids would be more difficult to manipulate, more difficult to introduce into cells and subject to more of the drawbacks described above in connection with whole proteins, including degradation and immunological intolerance.

It will be appreciated that 20 amino acid peptides containing one or more amino acid substitutions in various positions of the sequence shown in SEQ ID NO:1 are also within the scope of the invention. Many amino acid substitutions can be made to the native 20-mer sequence and retain the activity of the peptide. However, in the preferred embodiment of the invention, the asparagine, glutamine, glycine and glycine residues at positions 193, 194, 211, and 212 of native RecA, respectively, are present in the corresponding positions of the peptides of the invention (positions 1, 2, 19 and 20), as these residues are highly conserved among RecA-like proteins. Moreover, the presence of the aromatic amino acids phenylalanine, tyrosine or tryptophan at position 203 is also preferred.

Variations of SEQ ID NO: 1 contemplated for use in the present invention include minor insertions, deletions or substitutions that do not substantially affect its ability to bind and unstack DNA and to catalyze the formation of joint ssDNA-dsDNA molecules. For example, conservative amino acid replacements are contemplated. Such replacements are, for example, those that take place within a family of amino acids that are related in their side chains. The families of amino acids include the acidic amino acids (aspartic acid, glutamic acid); the basic amino acids (lysine, arginine, histidine); the non-polar amino acids (alanine, valine, leucine, isoleucine, proline, phenylalanine, methionine, tryptophan; and the uncharged polar amino acids (glycine, asparagine, glutamine, cysteine, serine threonine, tyrosine); and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site will not have a major effect on the properties of the polypeptide.

In fact, any peptide derivative of SEQ ID NO:1, including conservative substitutions, non-conservative substitutions, mixtures thereof, as well as truncated peptides and longer peptide sequences containing additional amino acids of native RecA or sequence variations thereof may be tested as described in the examples set forth hereinbelow to determine their ability to bind ssDNA/dsDNA, unstack ssDNA and catalyze joint ssDNA-dsDNA molecule formation. Such routine experimentation will allow the skilled artisan to easily screen any desired peptide.

The peptides of the invention bind to both ssDNA and dsDNA in vitro, both in the presence and absence of magnesium ion as evidenced by a filter binding assay, as described below in Example 2.

EXAMPLE 2 ssDNA and dsDNA Binding Assays dsDNA was prepared by annealing of 5' $^{32}$P labeled oligonucleotide BS-S1 (5'-GGCCGCTCTAGAACTAGTGGAT CCCCCGGGCTG-CAGGAATTCGATATCA AGCT-3'; SEQ ID NO:8) and unlabeled BS-S2 (5'-AGCTTGATATCGAATTCCTGCAGC-CCGGGGATCCACTAGTTCTAGAGCGG CC-3'; SEQ ID NO:9). BS-S1 spans positions 742–690 in the polylinker region of the plasmid Bluescript SK$^+$ (Stratagene, La Jolla, Calif.) and BS-S2 is the complement of BS-S1. Binding Reactions were performed in a volume of 40 µl and contained $^{32}$P-labeled 0.5 µm ssDNA or 1 µm dsDNA (expressed as phosphate concentration), 40 mM Tris-borate, pH 7.5, 0 or 10 mM MgCl$_2$, 20 mM NaCl, 10 µg/ml BSA, 10 mM CAPS, pH 10.6 and peptide concentrations of up to 100 µm; final pH value was 8.3. After a 30 minute incubation at room temperature, reaction mixtures were filtered using a double-filter system (Wong et al., Proc. Natl. Acad. Sci. USA, 90:5428–5432, 1993) with BA85 nitrocellulose filters and NA45 DEAE membranes (Schleicher and Schuell, Keene, N.H.). All experiments were performed in at least triplicate. Data were quantitated with a phosphorimager (Molecular Dynamics).

Figure 1C:
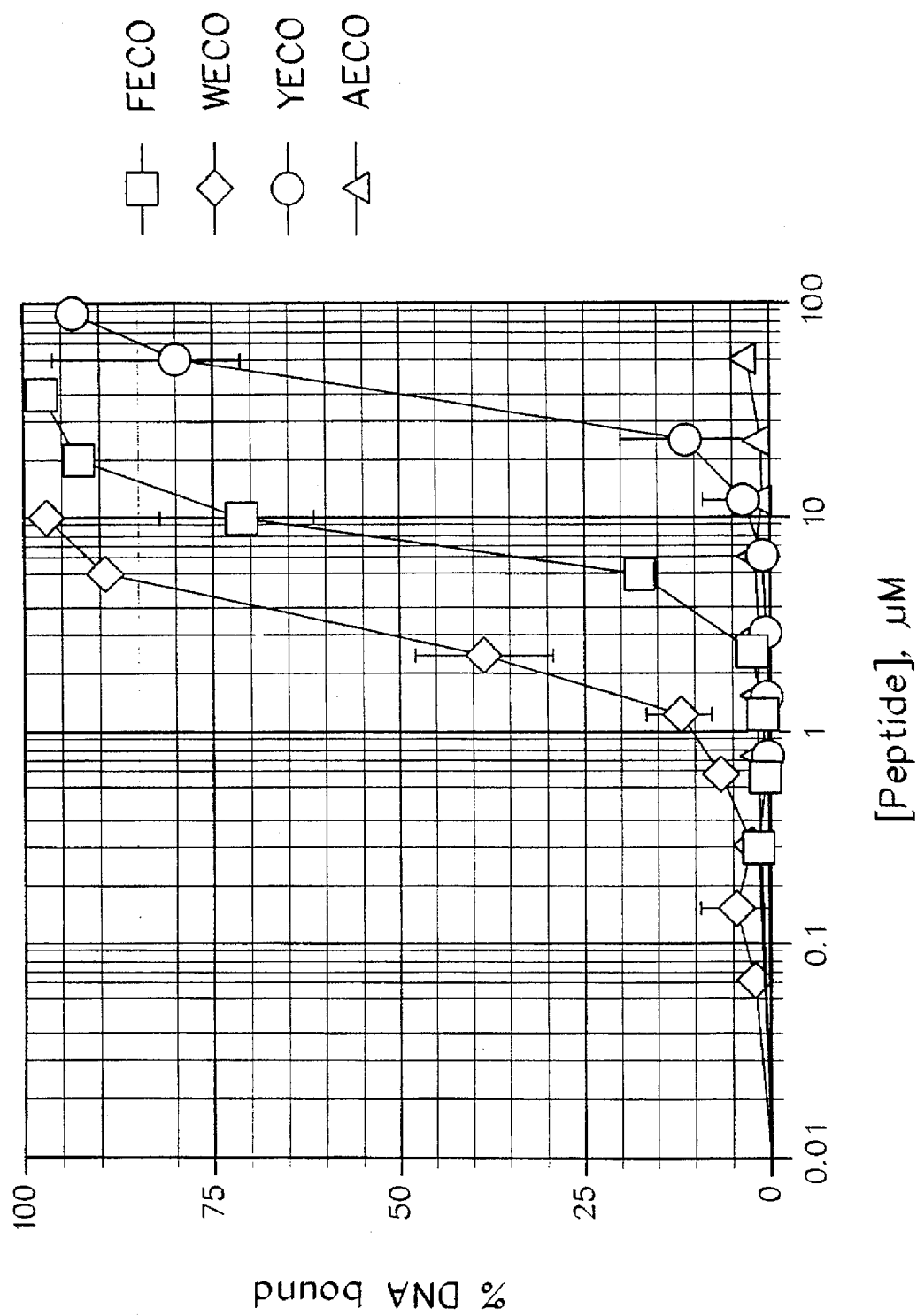
FIG. 1c illustrates binding of the FECO, WECO, YECO and AECO to dsDNA (1.0 µM) in the presence of 10 mM $MgCl_2$. The peptide concentration is shown on the x-axis and the percentage of dsDNA bound is shown on the y-axis.
Figure 1D:
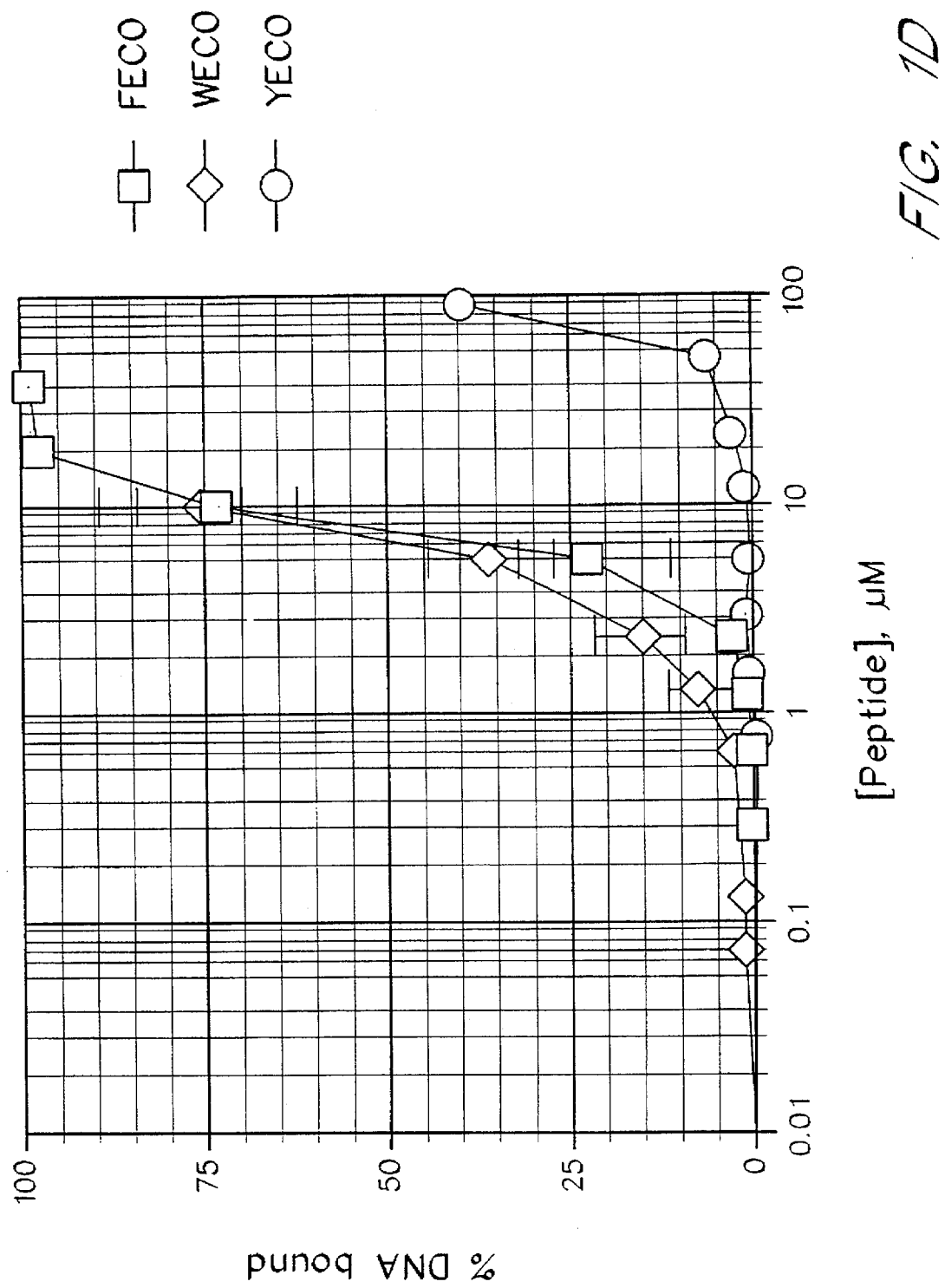
FIG. 1d illustrates binding of the FECO, WECO and YECO to ssDNA (0.5 µM) in the absence of $MgCl_2$. The peptide concentration is shown on the x-axis and the percentage of ssDNA bound is shown on the y-axis.
Figure 1E:
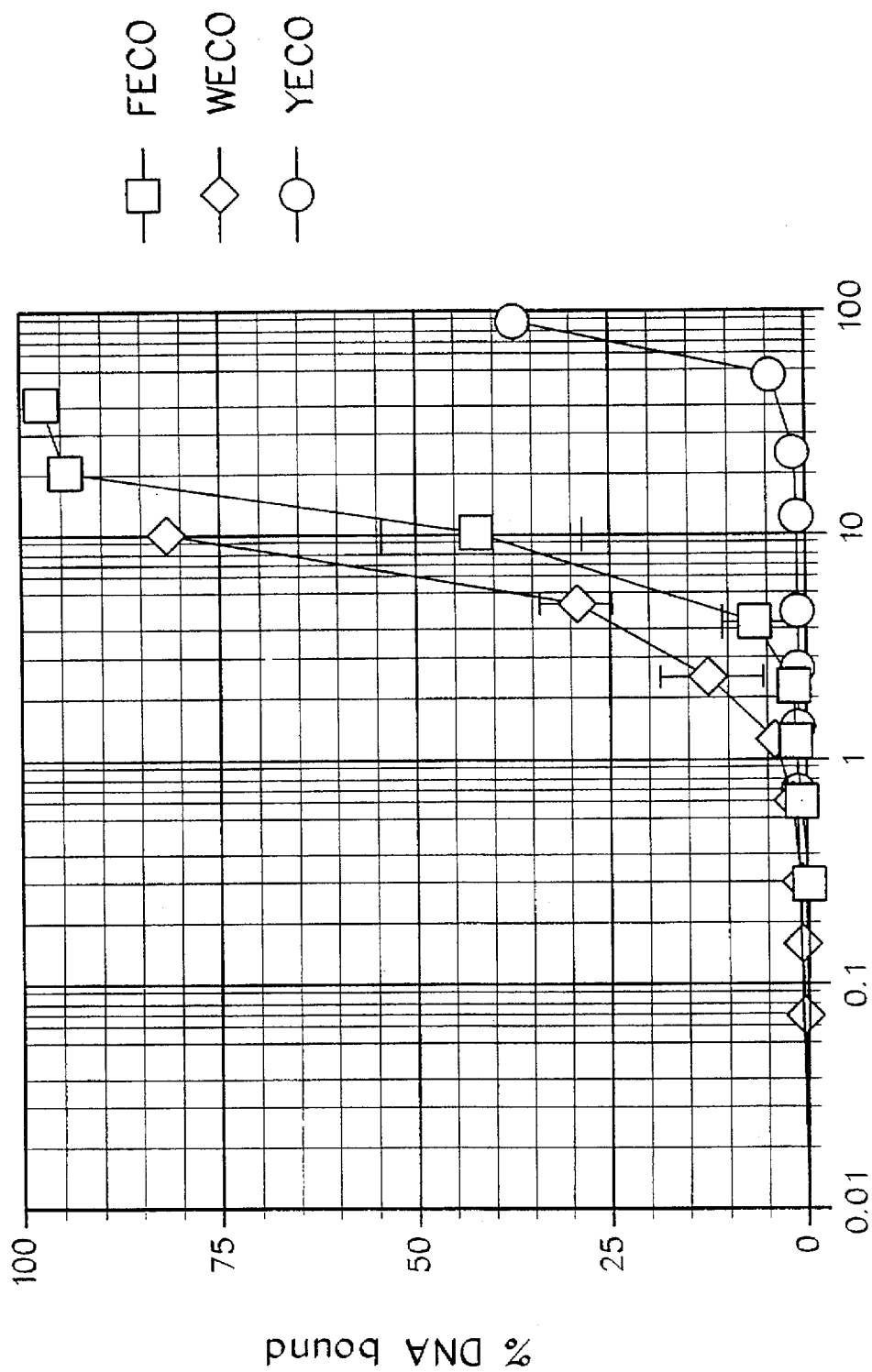
FIG. 1e illustrates binding of the FECO, WECO and YECO to dsDNA (1.0 µM) in the absence of $MgCl_2$. The peptide concentration is shown on the x-axis and the percentage of dsDNA bound is shown on the y-axis.

The results shown in FIGS. 1b and 1c indicate that an aromatic amino acid (phenylalanine, tyrosine or tryptophan) is needed at amino acid position 203 of RecA (amino acid 11 of SEQ ID NOS: 1–4) for binding to both ssDNA and dsDNA. The sequence shown in SEQ ID NO:4 in which residue 11 is an alanine did not bind to either ssDNA or dsDNA (FIG. 1b, c). Further, HECO, WT-14 and WT-Scr did not bind to either ssDNA or dsDNA. WT-Scr contains the same amino acid composition as FECO, but in a scrambled sequence. The phenylalanine residue at position 203 is the most conserved internal position among prokaryotic RecA proteins and their eukaryotic homologs, such as Dmc1 and Rad51 (Story et al., Science, 259:1892–1896, 1993). Although the peptides bind less tightly in the absence of magnesium ions than in their presence (FIGS. 1d, e), the fact that 100–200 mM NaCl can substitute for 10 mM Mg$^{2+}$ indicates that this is not a specific divalent ion effect. As expected, ATP, ADP and ATPγS had no effect on binding of the peptides to DNA.

The peptides promote unstacking of DNA as assessed by increased sensitivity of thymine residues to the modifying reagent potassium permanganate. The ability of the aromatic amino acid-containing peptides to unstack DNA was addressed as described in the following example.

EXAMPLE 3

Assay for Unstacking Ability

RecA is known to extend both ssDNA and dsDNA by 50% (Koller et al., in Mechanisms of DNA Replication and Recombination, N. Cozzarelli, Ed., Alan R. Liss, Inc., New York, 723–729, 1983). The unstacking of the ssDNA is proposed to be essential for RecA-mediated DNA triplex formation between ssDNA and ds DNA (Camerini-Otero et al., Cell, 73:217–223, 1993). Unstacked bases are more accessible to modification by potassium permanganate (PP), an agent that attacks thymines in a direction perpendicular to the base plane (Hayatsu et al., Biochem. Biophys. Res. Commun., 29:556–561, 1967). This modification is monitored by chemically-induced strand cleavage at the modified base (Maxam et al., Meth. Enzymol., 65:499–560, 1980).

Peptide-DNA complexes were prepared as described in Example 2, in a total volume of either 100 or 140 µl. In the latter case, 40 µl was used for filter binding and the remainder treated with PP. To bind RecA protein to BS-S1, 2.7 µm RecA and 0.5 µm $^{32}$P-labeled BS-S1 were incubated in a volume of 100 µl containing 25 mM Tris-Hcl, pH 7.5, 10 mM MgCl$_2$, 20 mM NaCl, 0.4 mM dithiothreitol (DTT), 0.5 mM EDTA, 0.3 mM ATPγS, 1.1 mM ADP and 10 µg/ml BSA for 30 min. at 37° C. Complexes were incubated with 0.5 mM PP for 1 min. at room temperature. Reactions were terminated with DMS-stop solution (Maxam et al., ibid.) and precipitated with ethanol. After treatment with 1M pyrollidone (95° C., 20 min.), the samples were separated on a polyacrylamide gel containing 20% urea (Sequagel, National Diagnostic). The gel was dried and exposed to x-ray film.

As expected, the ss oligonucleotide was much more reactive to PP in the presence of RecA than in its absence, as illustrated by the higher intensities of the bands. Peptides FECO and WECO induced pronounced hypermodification of thymine residues in the ssDNA. As a result, little if any full size fragments remain and most of the radioactivity is found in very short oligonucleotides, suggesting multiple hits by PP. The reactivity of the ssDNA to PP was also increased in the presence of YECO, but to a lesser extent than FECO and WECO. The shuffled non-DNA-binding WT-Scr peptide had no effect. These results indicate that, as with intact RecA, WECO and FECO unstack ssDNA upon binding thereto.

The extent of modification of the thymine residues in the ssDNA increased with FECO concentration in a manner which paralleled the binding profile. Interestingly, although the binding of FECO to dsDNA was similar to that for ssDNA, no distinct modification of dsDNA was observed using peptide concentrations between 0 and 25 µm. This suggests that the peptide uses different modes in binding to ssDNA versus dsDNA and that binding to dsDNA does not occur at single-stranded regions in the duplex.

The structure of the peptides themselves is changed upon binding to DNA as assessed by circular dichroism spectroscopy. In the absence of DNA, the peptides assume a random-coil conformation. However, upon DNA binding, the peptides shift from random-coil structure to β-sheet. This conformational change appears important in binding to ssDNA and dsDNA and unstacking the ssDNA.

Because the structure of the DNA changed upon peptide binding, the ability of the peptides to change their secondary structure (conformation) upon binding to DNA was investigated using CD spectroscopy as described below.

EXAMPLE 4

CD Spectroscopy of Peptides and Peptide-DNA Complexes

CD spectroscopy measures protein and nucleic acid secondary structure. All CD spectra were measured using a Jasco 720 spectropolarimeter. The instrument was calibrated with a 0.06% ammonium (+)-$d_{10}$-camphorsulphate solution which generated a CD intensity of 190.4 millidegrees (mdeg) at 290.4 nm. A baseline of 10 mM $NaH_2PO_4$ buffer was subtracted out as background. Cells of 0.20, 0.50 or 1.00 mm pathlength were used and maintained at 22±1° C. The response and band width for data collection were 2.0 sec and 1.0 nm, respectively. Spectra were smoothed using Savitsky Golay smooth and are presented at 2 nm interval and in molar residue ellipticity (degree*$M^{-1}$*$cm^{-1}$) or as raw data (mdeg).

Figure 2A:
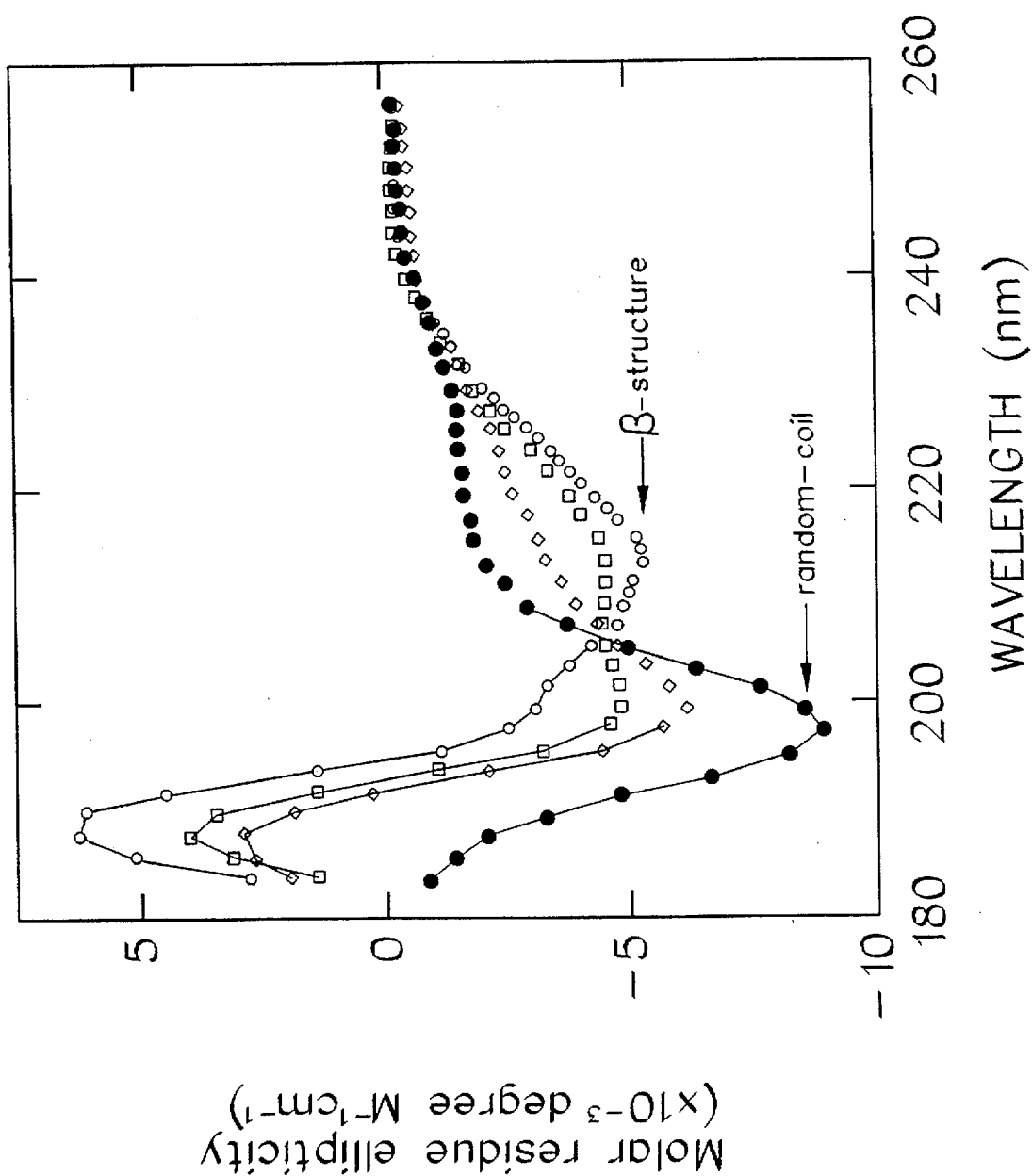
FIG. 2a illustrates a circular dichroism (CD) spectrum of a reaction mixture in which a 57-mer ssDNA molecule (CTGTCTACTCTCGAGGTTAACCCGTGCGAATTCTA-CGATTGGTGCGGCCGGT ATATC; SEQ ID NO:7; 0.3 mM) was incubated at pH 7.5±0.2 in the presence of 0.1 mM FECO (○) or with FECO at concentrations of 0.20 mM (◇), 0.25 mM (□) and 0.40 mM (△).

As shown in FIG. 2a, binding of FECO to ssDNA induced a conformational transition from random coil to mostly β-structure. While the dominant negative CD peak at approximately 198 nm at low peptide concentration indicated a random-coil structure, the amplitude increase at both 190 nm and 215 nm at higher peptide concentrations is characteristic of a concentration-dependent binding of a structure with a high β-structure content on the DNA (Woody et al., in The Peptides, Analysis, Synthesis, Biology, V. Hruby, Ed., Academic Press, Inc., New York, 1985, pp. 15-114). The peptide remains a random coil in the absence of DNA, even at higher peptide concentrations. The isodichroic point of 207 nm indicates that the data can best be described as a transition between two, and not more, states.

Figure 2C:
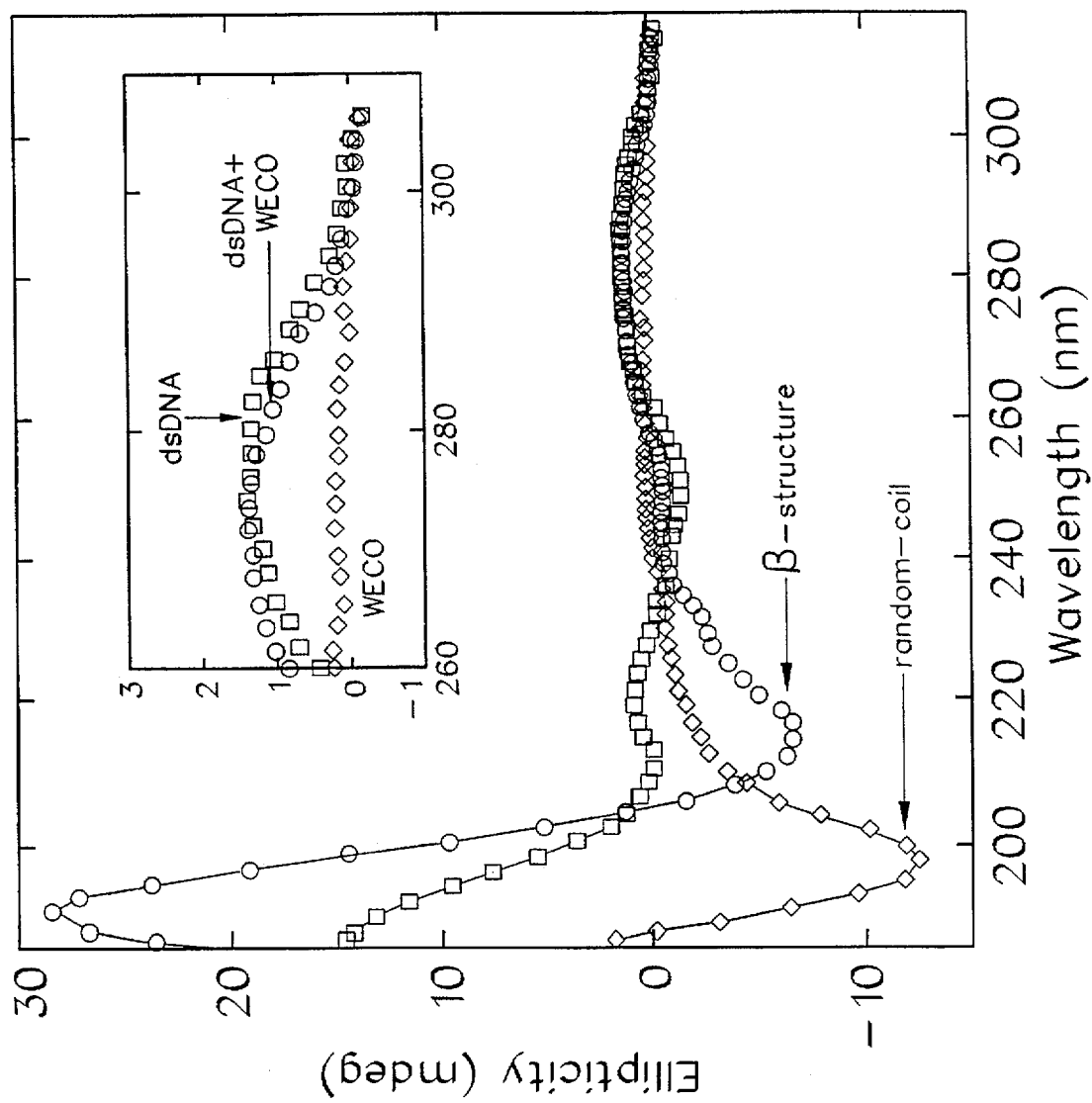
FIG. 2c illustrates a CD spectrum of 0.10 mM WECO in the presence (○) or absence (◇) of 0.40 mM dsDNA from the HaeIII digestion products of plasmid pUC18 at pH 6.0±0.2. The inset shows the enlargement of the spectral region from 260–300 nm to emphasize lack of the intensity change at 278 nm.
Figure 2D:
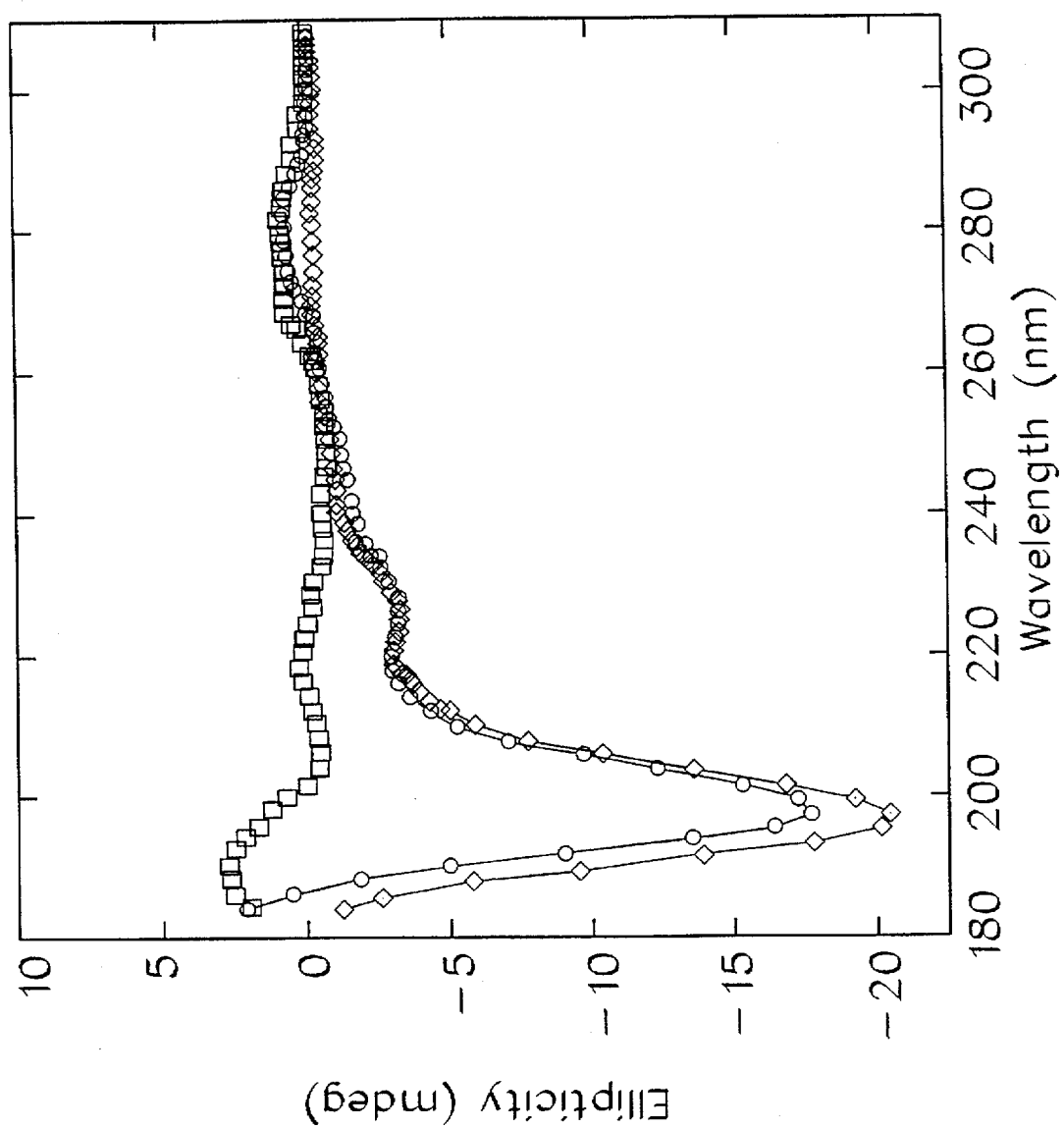
FIG. 2d illustrates a CD spectrum of 0.40 mM HECO in the presence (○) and absence (◊) of 0.4 mM ssDNA at pH 7.5±0.2.

A similar structural change is also evident in WECO (FIG. 2b). However, WECO forms a more complete β-structure than FECO under the same conditions, most likely due to its higher affinity for DNA. All other peptides tested remained predominantly random coil structures in the presence of ssDNA, as typified by the HECO CD profile (FIG. 2d). In addition, the reduction in the 278 nm DNA band for the WECO-ssDNA complex (FIG. 2b, inset) supports the chemical modification data showing that the ssDNA is unstacked upon complex formation. Binding to dsDNA also induces β structure in WECO but, consistent with the chemical modification data, results in only minor changes in the 278 nm band (FIG. 2c).

The CD changes correlate well with the filter binding and chemical modification data, suggesting that CD and these methods are complementary and that the conformational change of the peptide from random coil to β structure is important in binding to ssDNA and dsDNA and unstacking the ssDNA.

Most importantly, the peptides of the invention promote joint molecule formation between ssDNA and dsDNA molecules having one or more regions of homology. The formation of joint molecules by the peptides does not require an external energy source, as nucleotide cofactors are unnecessary. This has also been demonstrated for RecA. It is contemplated that this joint molecule formation results in homologous DNA recombination and subsequent heteroduplex formation.

The ability of the peptides of the invention to promote homologous pairing of DNA molecules will allow introduction of a nucleic acid sequence into a precise location in the human genome. In a preferred embodiment, the peptide and a ssDNA sequence having homology to a particular sequence contained within the genome are introduced into particular cells in vivo. This may be accomplished, for example, by encapsulating the peptide and ssDNA in a liposome followed by injection into the bloodstream. The liposomes will fuse with cells in vivo, resulting in intracellular delivery of peptide and ssDNA sequence. The ssDNA sequence will then pair with its corresponding genomic sequence, forming a ssDNA-dsDNA three-stranded molecule. Alternatively, the peptide and ssDNA sequence may be directly coinjected. Because the peptide is small, there is reduced risk of a substantial immunological response compared to a large protein such as RecA which would elicit a substantial immune response. In addition, the peptide may be chemically modified by well known techniques to increase its stability.

RecA can bring together any two homologous DNA molecules and promote their recombination. Although FECO and WECO both bind ssDNA and dsDNA, assume a well-defined structure as a result of this binding, and unstack ssDNA, it would be unexpected that such short 20 amino acid peptides would selectively pair a ssDNA with a homologous dsDNA. This possibility was addressed in the following example.

EXAMPLE 5

Homologous DNA Pairing by RecA-derived Peptides

The formation of joint (ssDNA-dsDNA) molecules was investigated by incubating 300 ng pBluescript $KS^+$ (supercoiled plasmid) and 13 ng $^{32}$P-BS-S1 with either 13.6 µm RecA or 50 µm peptide under conditions used for RecA and peptide-ssDNA formation described in Example 3, with the exception that reactions involving peptides were allowed to proceed for 90 min. at 45° C. The ratio between ss oligonucleotides and the target ds DNA sequence was 9-10 oligonucleotides per dsDNA molecule for both the peptide and RecA reactions. Reactions were quenched by the addition of 2% sodium dodecyl sulfate (SDS) and 20 mM EDTA, followed by electrophoresis on a 1% agarose gel containing 6 mM magnesium acetate and 0.5 µg/ml ethidium bromide for 4 hours in a cold room. The gel was dried and exposed to x-ray film.

Surprisingly, FECO and WECO catalyzed the formation of stable joint ssDNA-dsDNA (BS-S1/pBluescript) molecules similar to those formed by RecA. These joint molecules are detected as comigration of radiolabel with the plasmid on the agarose gel. We were able to recover from 10% to 20% as many joint molecules from reactions with these two peptides compared to the whole RecA protein. No joint molecules were formed when BS-S1 was replaced with a duplex having the same sequence or when a target plasmid lacking a region homologous to BS-S1, pUC19, was used. YECO, which binds poorly to DNA, and other peptides which do not bind to DNA, did not promote formation of joint ssDNA-dsDNA molecules. As mentioned hereinabove, these peptides can form homology-dependent stable joint molecules in the absence of a nucleotide cofactor. Thus, this experiment illustrates the selective targeting of a ssDNA molecule to its complementary region on a dsDNA molecule.

The fact that DNA binding peptides derived from RecA are able to form joint molecules between homologous DNAs indicates that this domain comprises at least part of the active site of the whole protein responsible for DNA pairing. That the reaction proceeds efficiently in the absence of the remainder of the protein and in the absence of nucleotide cofactors or their analogs suggests that a major role of the remainder of the protein, in addition to its other biochemical activities, is to modulate access to this pairing domain in a nucleotide cofactor-dependent manner.

This DNA targeting technique is also valuable in correcting a mutant gene sequence characteristic of many genetic disorders. Examples of genetic disorders believed correctable through this technique include sickle cell anemia, β-thalassemia, cystic fibrosis, muscular dystrophy and the like. The complementary (wild type) ssDNA sequence will contain the correct nucleotide(s) at the position(s) in the mutant dsDNA sequence which contains the mutation. The wild type sequence will then complement the mutation, resulting in expression of a normal protein.

This technique will also allow the modulation of gene expression in a fashion similar to triplex approaches for antigene therapies. In these triplex therapies, the introduced oligonucleotide binds to the coding strand of a particular gene sequence, inhibiting its transcription into mRNA in the nucleus. Similarly, the ssDNA molecule may be targeted by the peptides of the invention to a particular gene sequence for three stranded DNA formation and inhibition of transcription. In addition, gene sequences which encode regulatory proteins which either stimulate or inhibit the transcription of other genes may be targeted using the peptides of the invention. For example, if a gene encodes a product which stimulates transcription of an undesirable gene, the gene encoding the product may be targeted for three-stranded DNA formation in vivo.

The peptides of the invention may be used to promote inhibition of transcription of oncogenes and deleterious viral transcription products by promoting joint molecule formation between these genes and ssDNA molecules having homology to regions thereof. For example, the p190$^{BCR-Abl}$ gene occurring in chronic myelogenous leukemia (CML) or acute lymphoblastic leukemia (ALL) may be targeted with a ssDNA complementary thereto, resulting in three-stranded DNA formation and inhibition of its transcription. The ras oncogene is known to be present in a variety of human tumor types and may play a major role in tumorigenesis. This oncogene may be targeted with its complementary sequence, or a fragment thereof, using the instant peptides. Similarly, vital transcription products encoded by many problematic human viruses could also be targeted, including the reverse transcriptase gene of retroviruses and nucleocapsid proteins of hepatitis virus, rabies virus or any other desired virus.

In another preferred embodiment, cells are removed from a patient and transfected ex vivo with a peptide of the invention in combination with a desired wild-type ssDNA having homology to a region of a mutant gene sequence(s). The introduction of this wild-type sequence will result in the formation of a three-stranded DNA molecule at the region of homology between the ssDNA and ds DNA, thus complementing the mutant sequence(s), resulting in production of a functional gene product. Transfection may be performed using any of a variety of well known techniques including, but not limited to, electroporation, calcium phosphate DNA precipitation and DEAE-dextran. The cells are then expanded in culture, preferably in the presence of a growth factor or cytokine, prior to reintroduction into the patient. This technique is particularly useful in genetic abnormalities expressed in blood cells, such as sickle cell anemia, thalassemias, and the like. However, the technique can also be used to correct other genetic abnormalities through reintroduction of cells bearing the wild type gene or gene fragment. In a particularly preferred embodiment, the wild type gene is introduced into bone marrow stem cells for the treatment of blood cell genetic abnormalities. The desired cells are then isolated from the transfected mixture and reintroduced into the marrow of the patient.

Examples of the use of peptides of the invention to promote DNA pairing to complement a genetic defect are described below in Examples 6 and 7.

EXAMPLE 6

Treatment of Sickle Cell Anemia

Sickle cell anemia is a genetic disease characterized by cardiac enlargement, swelling of the lymph nodes and anemia. This disease is caused by a point mutation at position 6 of the β chain of hemoglobin in which a valine replaces the normally-occurring glutamate, markedly reducing the solubility of deoxygenated hemoglobin and resulting in sickling or polymerization of hemoglobin leading to sickling of red blood cells which blocks blood vessels, leading to local regions of low oxygen concentrations.

Red blood cell precursors cells are synthesized in the bone marrow and are responsive to the hormone erythropoietin (EPO). Bone marrow is isolated from a patient and the cells contained therein are cultured in a semi-solid matrix in the presence of EPO. After several days, colonies of about 60 erythrocytes appear, each founded by a single committed erythroid progenitor cell (Alberts et al., *Molecular Biology of the Cell*, Second Edition, Garland Publishing, Inc., New York, p. 980). This cell is known as an erythrocyte colony-forming cell, or CFC-E, and it gives rise to mature erythrocytes after about six division cycles or less. The CFC-E cells are isolated and cotransfected by electroporation with the peptide shown in SEQ ID NO: 1 and a portion of a wild type ssDNA strand encoding the β chain of hemoglobin which contains glutamate at position 6. The transfected cells are then injected back into the patient. The patient is then monitored for diminishing symptoms of the disease.

EXAMPLE 7

Treatment of Duchenne Muscular Dystrophy (DMD)

Duchenne Muscular dystrophy is a degenerative muscle wasting disease caused by mutations in the dystrophin gene. Patients with muscular dystrophy are given multiple injections of a preparation containing the functional dystrophin gene coding strand (Koenig et al., *Cell*, 53:219–226, 1988) and the peptide shown in SEQ ID NO:1. While under light anesthesia the patients are injected at 5 cm intervals into the entire skeletal muscle mass directly through the skin without surgery. Patient recovery is monitored by monitoring twitch tension and maximum voluntary muscle contraction.

EXAMPLE 8

Inhibition of p190$^{BCR-ABL}$ Transcription in Vivo

In patients with acute lymphoblastic leukemia (ALL), a reciprocal chromosomal translocation t(9:22) (q34:q11) results in a truncated chromosome 22, encoding at the breakpoint a fusion of sequences from the c-ABL protooncogene (Bartram, et al. *Nature*, 306:277–280, 1983) and the BCR gene (Groffen et al., *Cell*, 36:93–99, 1984). In ALL, the breakpoints usually occur in the first introns of both BCR and c-ABL, resulting in a p190$^{BCR-ABL}$ gene product (Kurzrock et al., *Nature*, 325:631–635, 1987).

White blood cells are isolated from patients with ALL. These cells are cotransfected by electroporation with the peptide shown in SEQ ID NO: 1 and a ssDNA complementary to the transcription initiation site of the p190$^{BCR-ABL}$ gene. The cells are expanded in culture, preferably in the presence of a cytokine or growth factor, then reintroduced into the patient. The patient is monitored over time for diminishing symptoms of the disease.

The ability to stimulate homologous recombination with well-defined short peptides of approximately 20 amino acids will allow the delivery of these peptides into cells in large quantities and with great facility, a task virtually impossible with whole protein molecules. These peptides may also be chemically modified using well known techniques to increase their stability and bioavailability, i.e., methylation, acylation, t-butylation and the like.

Another important use of the peptides of the invention is in the mapping and cloning of large complex genomes. The use of whole RecA for site-specific cleavage of DNA is currently being used in vitro for the mapping and cloning of the human genome and is discussed in copending application Ser. No. 08/089,910. Similarly, the peptides of the invention may also be used for site-specific cleavage of DNA to facilitate the mapping and cloning of complex genomes.

An additional use of the instant peptides is in the generation of transgenic animals and other organisms. A particular application would be in the development of transgenic mice. Mutations are generated in embryonic stem (ES) cells by homologous recombination between exogenously added DNA and the endogenous chromosomal sequences (Mansour, *GATA*, 7:219–227, 1990). Homologous recombination allows precise targeted insertion of genetic information, correction of gene mutations and gene inactivation; however, this homologous recombination is a rare, inefficient event. These cells are then used to generate chimeric intermediates that pass the mutant allele through the germ line, initiating a strain of mice that carry the desired mutation. This well known technique is disclosed in U.S. Pat. No. 4,736,866. Using this method, an extremely large number of transformed ES cells must be screened to determine which cell contains the exogenously added DNA. The frequency of precise DNA stable integration at the homologous DNA locus will be greatly increased by cotransfection of the instant peptides and the ssDNA of interest. The cotransfection of an exogenously added DNA molecule in the presence of the claimed peptides into ES cells will improve the speed and efficiency of the homologous recombination between the two DNA sequences, resulting in larger numbers of transformed ES cells containing the mutation, thus significantly reducing the number of cells to be screened.

Although the invention has been described with reference to particular preferred embodiments, the scope of the invention is defined by the following claims and should be construed to include reasonable equivalents.

We claim:

1. A peptide comprising at least 15 consecutive amino acids of the amino acid sequence shown in SEQ ID NO.1 or conservative amino acid substitutions thereof, said peptide being capable of promoting pairing of a single-stranded DNA molecule and a double-stranded DNA molecule, wherein said single-stranded DNA molecule is homologous to at least a portion of said double-stranded DNA molecule.

2. The peptide of claim 1, wherein said peptide has the amino acid sequence shown in SEQ ID NO:1.

3. The peptide of claim 1, wherein said peptide has an amino acid sequence selected from the group consisting of SEQ ID NO:2 and SEQ ID NO:3.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: FECO ( x i ) SEQUENCE DESCRIPTION: SEQ ID NO:1:

```
Asn  Gln  Ile  Arg  Met  Lys  Ile  Gly  Val  Met  Phe  Gly  Asn  Pro  Glu  Thr
 1                  5                        10                       15
Thr  Thr  Gly  Gly
              20
```

( 2 ) INFORMATION FOR SEQ ID NO:2:

( i ) SEQUENCE CHARACTERISTICS:
        ( A ) LENGTH: 20 amino acids
        ( B ) TYPE: amino acid
        ( C ) STRANDEDNESS: single ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: WECO ( x i ) SEQUENCE DESCRIPTION: SEQ ID NO:2:

```
Asn Gln Ile Arg Met Lys Ile Gly Val Met Trp Gly Asn Pro Glu Thr
1               5                   10                  15
Thr Thr Gly Gly
            20
```

( 2 ) INFORMATION FOR SEQ ID NO:3:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: YECO ( x i ) SEQUENCE DESCRIPTION: SEQ ID NO:3:

```
Asn Gln Ile Arg Met Lys Ile Gly Val Met Tyr Gly Asn Pro Glu Thr
1               5                   10                  15
Thr Thr Gly Gly
            20
```

( 2 ) INFORMATION FOR SEQ ID NO:4:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: HECO ( x i ) SEQUENCE DESCRIPTION: SEQ ID NO:4:

```
Asn Gln Ile Arg Met Lys Ile Gly Val Met His Gly Asn Pro Glu Thr
1               5                   10                  15
Thr Thr Gly Gly
            20
```

( 2 ) INFORMATION FOR SEQ ID NO:5:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
    ( B ) CLONE: AECO ( x i ) SEQUENCE DESCRIPTION: SEQ ID NO:5:

```
Asn Gln Ile Arg Met Lys Ile Gly Val Met Ala Gly Asn Pro Glu Thr
1               5                   10                  15
Thr Thr Gly Gly
            20
```

( 2 ) INFORMATION FOR SEQ ID NO:6:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: WT-14

( x i ) SEQUENCE DESCRIPTION: SEQ ID NO:6:

```
Arg Met Lys Ile Gly Val Met Phe Gly Asn Pro Glu Thr Thr
1               5                   10
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i i ) IMMEDIATE SOURCE:
        ( B ) CLONE: WT-Scr ( x i ) SEQUENCE DESCRIPTION: SEQ ID NO:7:

```
Ile Pro Glu Gln Thr Lys Gly Gly Arg Asn Thr Met Asn Val Phe Gly
1               5                   10                  15
Met Gly Ile Thr
            20
```

( 2 ) INFORMATION FOR SEQ ID NO:8:

( i ) SEQUENCE CHARACTERISTICS:
  ( A ) LENGTH: 57 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
  ( B ) CLONE: 57-mer ( x i ) SEQUENCE DESCRIPTION: SEQ ID NO:8:

CTGTCTACTC TCGAGGTTAA CCCGTGCGAA TTCTACGATT GGTGCGGCCG GTATATC　　　57

( 2 ) INFORMATION FOR SEQ ID NO:9:

( i ) SEQUENCE CHARACTERISTICS:
  ( A ) LENGTH: 53 base pairs
  ( B ) TYPE: nucleic acid
  ( C ) STRANDEDNESS: single
  ( D ) TOPOLOGY: linear ( i i ) MOLECULE TYPE: cDNA ( i i i ) HYPOTHETICAL: NO ( i v ) ANTI-SENSE: NO ( v i i ) IMMEDIATE SOURCE:
  ( B ) CLONE: BS-S1

( x i ) SEQUENCE DESCRIPTION: SEQ ID NO:9:

GGCCGCTCTA GAACTAGTGG ATCCCCCGGG CTGCAGGAAT TCGATATCAA GCT　　　53